United States Patent
Prencipe et al.

(10) Patent No.: US 11,234,915 B2
(45) Date of Patent: *Feb. 1, 2022

(54) ORAL CARE COMPOSITIONS AND METHODS OF USE

(71) Applicant: Colgate-Palmolive Company, New York, NY (US)

(72) Inventors: Michael Prencipe, West Windsor, NJ (US); Amy Russo, Belle Mead, NJ (US); Hansruedi Stettler, Basel (CH); Betty Won, Princeton Junction, NJ (US); Lisa Manus, Lawrenceville, NJ (US); Michael Stranick, Bridgewater, NJ (US); Peng Yan, Guangzhou (CN); Chengkang Tan, Guangzhou (CN); Vyoma Patel, Hillsborough, NJ (US); André Morgan, Robbinsville, NJ (US); Andrei Potanin, Hillsborough, NJ (US); Xiao Yi Huang, Guangzhou (CN)

(73) Assignee: Colgate-Palmolive Company, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/815,106

(22) Filed: Mar. 11, 2020

(65) Prior Publication Data

US 2020/0206116 A1 Jul. 2, 2020

Related U.S. Application Data

(63) Continuation of application No. 15/559,507, filed as application No. PCT/CN2016/086994 on Jun. 24, 2016, now Pat. No. 10,617,620.

(51) Int. Cl.
| | |
|---|---|
| *A61Q 11/00* | (2006.01) |
| *A61K 8/27* | (2006.01) |
| *A61K 8/21* | (2006.01) |
| *A61K 8/25* | (2006.01) |
| *A61K 33/30* | (2006.01) |
| *A61K 33/16* | (2006.01) |
| *A61K 6/00* | (2020.01) |
| *A61K 31/198* | (2006.01) |
| *A61K 8/44* | (2006.01) |
| *A61K 8/24* | (2006.01) |
| *A61K 8/73* | (2006.01) |
| *A61K 8/04* | (2006.01) |
| *A61K 8/37* | (2006.01) |
| *A61K 8/34* | (2006.01) |
| *A61K 8/365* | (2006.01) |

(52) U.S. Cl.
CPC ........... *A61K 8/44* (2013.01); *A61K 8/042* (2013.01); *A61K 8/21* (2013.01); *A61K 8/24* (2013.01); *A61K 8/25* (2013.01); *A61K 8/27* (2013.01); *A61K 8/34* (2013.01); *A61K 8/365* (2013.01); *A61K 8/37* (2013.01); *A61K 8/442* (2013.01); *A61K 8/73* (2013.01); *A61K 8/731* (2013.01); *A61Q 11/00* (2013.01); *A61K 2800/28* (2013.01); *A61K 2800/48* (2013.01); *A61K 2800/52* (2013.01)

(58) Field of Classification Search
CPC . A61Q 11/00; A61K 8/27; A61K 8/25; A61K 8/21; A61K 2800/92; A61K 2300/00; A61K 33/30; A61K 33/16; A61K 47/183
See application file for complete search history.

(56) References Cited

U.S. PATENT DOCUMENTS

| | | | |
|---|---|---|---|
| 2,876,166 | A | 3/1959 | Nebergall |
| 2,946,725 | A | 7/1960 | Norris et al. |
| 3,095,356 | A | 6/1963 | Moss |
| 3,852,414 | A | 12/1974 | Adler et al. |
| 3,914,404 | A | 10/1975 | Langer |
| 4,335,102 | A | 6/1982 | Nakashima et al. |
| 4,469,674 | A | 9/1984 | Shah et al. |
| 4,961,924 | A | 10/1990 | Suhonen |
| 5,000,944 | A | 3/1991 | Prencipe et al. |
| 5,017,363 | A | 5/1991 | Suhonen |
| 5,094,842 | A | 3/1992 | Riley |
| 5,096,702 | A | 3/1992 | Rolla et al. |
| 5,188,820 | A | 2/1993 | Cummins et al. |
| 5,244,652 | A | 9/1993 | Michaels |
| 5,258,173 | A | 11/1993 | Waterfield |
| 5,716,600 | A | 2/1998 | Zahradnik et al. |
| 5,833,952 | A | 11/1998 | Grigor et al. |
| 5,932,192 | A | 8/1999 | Campbell et al. |

(Continued)

FOREIGN PATENT DOCUMENTS

| | | |
|---|---|---|
| CA | 1136991 | 12/1982 |
| CA | 2026907 | 4/1991 |

(Continued)

OTHER PUBLICATIONS

Author Unknown, Colgate Enamel Health Whitening Toothpaste, Clean Mint Paste 5.5 oz (155g), drugstore.com, http://www.drugstore.com/colgate-enamel-health-whitening-toothpaste-clean-mint-paste/qxp532832?catid=183827, redirects to https://www.walgreens.com/store/c/colgate-enamel-health-whitening-toothpaste-clean-mint-paste/ID=prod6238066-product?dscmredirect=1, accessed Jul. 31, 2017.

Campbell, 2011, "Modern Stannous Fluoride Dentrifice: Q&A's for Dental Professionals," Hygiene Success, Catalyst Magazine, Issue 3, pp. 36-37.

Friberg, 1989, "Foam Stability in a Glycerol System," Journal of Colloid and Interface Science 127(2):573-582.

Huber Engineered Materials, "Guidelines for Choosing a Huber Cleaning Silica," http://www.hubermaterials.com/products/silica-and-silicates/dental-silicas/formulation-considerations/guidelines-for-choosing-a-huber-dental-cleaning-silica.aspx, accessed Mar. 25, 2015.

(Continued)

*Primary Examiner* — Tracy Liu

(57) ABSTRACT

This invention relates to oral care compositions comprising arginine or lysine, zinc citrate and zinc oxide, fluoride source, and a silica abrasive which exhibits an acid pH when measured as an aqueous slurry as well as to methods of using and of making these compositions.

17 Claims, No Drawings

(56) References Cited

U.S. PATENT DOCUMENTS

| | | |
|---|---|---|
| 6,187,295 B1 | 2/2001 | Glandorf |
| 6,464,963 B1 | 10/2002 | Gambogi et al. |
| 6,652,841 B1 | 11/2003 | Brown et al. |
| 6,685,920 B2 | 2/2004 | Baig et al. |
| 6,696,045 B2 | 2/2004 | Yue et al. |
| 8,211,406 B2 | 7/2012 | Baig et al. |
| 8,691,190 B2 | 4/2014 | Haught et al. |
| 8,778,311 B2 | 7/2014 | Regner |
| 8,906,347 B2 | 12/2014 | Strand et al. |
| 8,956,593 B2 | 2/2015 | Burgess et al. |
| 9,308,158 B2 | 4/2016 | Chandrasekaran et al. |
| 9,486,396 B2 | 11/2016 | Maloney et al. |
| 9,566,226 B2 | 2/2017 | Midha et al. |
| 9,687,427 B2 | 6/2017 | Li |
| 9,968,803 B2 | 5/2018 | Fruge et al. |
| 9,974,723 B2 | 5/2018 | D'Ambrogio |
| 9,980,890 B2 | 5/2018 | Pan et al. |
| 10,058,493 B2 | 8/2018 | Manus et al. |
| 10,098,829 B2 | 10/2018 | Fisher et al. |
| 2004/0146466 A1 | 7/2004 | Baig et al. |
| 2004/0258631 A1 | 12/2004 | Boyd et al. |
| 2007/0025928 A1 | 2/2007 | Glandorf et al. |
| 2008/0138298 A1 | 6/2008 | Glandorf et al. |
| 2009/0202454 A1 | 8/2009 | Mello et al. |
| 2013/0071456 A1 | 3/2013 | Fruge et al. |
| 2013/0209375 A1 | 8/2013 | Moya Argilagos et al. |
| 2013/0216485 A1 | 8/2013 | Campbell et al. |
| 2014/0314690 A1 | 10/2014 | Fisher et al. |
| 2015/0297500 A1 | 10/2015 | Robinson et al. |
| 2015/0305993 A1 | 10/2015 | Rege et al. |
| 2015/0313813 A1 | 11/2015 | Rege et al. |
| 2016/0303010 A1 | 10/2016 | Prencipe et al. |
| 2016/0338921 A1 | 11/2016 | Prencipe et al. |
| 2017/0348550 A1 | 12/2017 | Wilbens |
| 2018/0015016 A1 | 1/2018 | Huang et al. |
| 2018/0021234 A1 | 1/2018 | Prencipe et al. |
| 2018/0344596 A1 | 12/2018 | Manus et al. |

FOREIGN PATENT DOCUMENTS

| | | |
|---|---|---|
| CA | 2634758 | 7/2007 |
| CA | 2760445 | 11/2010 |
| EP | 0658565 | 6/1995 |
| JP | H07304641 | 11/1995 |
| JP | 5573120 | 8/2014 |
| WO | 1998/002135 | 1/1998 |
| WO | 2014/088572 | 6/2014 |
| WO | 2014/088573 | 6/2014 |
| WO | 2014/088575 | 6/2014 |
| WO | 2014/098822 | 6/2014 |
| WO | 2014/100928 | 7/2014 |
| WO | 2015/094849 | 6/2015 |
| WO | 2016/058140 | 4/2016 |
| WO | 2016/105440 | 6/2016 |

OTHER PUBLICATIONS

International Search Report and Written Opinion of the International Searching Authority in International Application No. PCT/CN2016/086994, dated Mar. 29, 2017.

O'Neil, ed., et al., 2001, "Zinc Phosphate," The Merck Index 13th edition, p. 1812 Monograph No. 10205.

Qiu et al., 2016, Modern Cosmetic Science and Technology, published by China Light Industry Press, p. 1735.

ORAL CARE COMPOSITIONS AND METHODS OF USE

CROSS REFERENCE TO RELATED APPLICATIONS

This application is a continuation of U.S. patent application Ser. No. 15/559,507, filed Sep. 19, 2017, which is a national stage entry under 35 U.S.C. § 371 of International Patent Application No. PCT/CN2016/086994, filed on Jun. 24, 2016, the contents of each of which are incorporated herein by reference in their entireties.

FIELD

This invention relates to oral care compositions comprising arginine or lysine or salt thereof, zinc oxide and zinc citrate, a fluoride source, and a silica which exhibits an acid pH when measured as an aqueous slurry, as well as to methods of using and of making these compositions.

BACKGROUND

Commercially available arginine-based contains arginine bicarbonate and precipitated calcium carbonate. The carbonate ion is believed to have cariostatic properties, and the calcium is believed to form a complex with arginine to provide a protective effect.

Viscosity stability is an important aesthetic aspect for many oral care compositions. However, developing and improving viscosity can be challenging.

Accordingly, there is a need for improved formulations oral compositions comprising basic amino acids with acceptable viscosity.

BRIEF SUMMARY

It has been surprisingly found that a composition containing a silica abrasive which provides an acid pH when slurried with water unexpectedly provides viscosity stability over time in oral care compositions comprising an amino acid, e.g., arginine or lysine, and a zinc oxide and/or zinc citrate, selected at certain concentrations and amounts.

The current formulations offer the advantage of robust microbial protection and viscosity stability of the oral care composition and by allowing for formulations which use less zinc—which may have undesirable aesthetic qualities (e.g., poor taste). Without being bound by any theory, it is believed that the presence of silica abrasive which provides an acid pH when slurried with water stabilizes other formulation ingredients against degradation in the presence of the amino acid in a manner that silicas of neutral or basic pH do not provide.

In one aspect the invention is an oral care composition (Composition 1.0) comprising:
a. A basic amino acid in free or salt from, wherein the amino acid is selected from arginine, lysine, and combinations thereof; (e.g., free form arginine);
b. zinc oxide and zinc citrate;
c. a fluoride source (e.g., sodium fluoride); and
d. a silica abrasive which exhibits an acid pH when measured as an aqueous slurry (e.g., prophy silica).

For example, the invention contemplates any of the following compositions (unless otherwise indicated, values are given as percentage of the overall weight of the composition):

1.01 Composition 1.0 wherein the silica abrasive which exhibits an acid pH when measured as an aqueous slurry is prophy silica.
1.02 Any of the preceding compositions wherein the silica abrasive which exhibits an acid pH when measured as an aqueous slurry is Sylodent 783.
1.03 Any of the preceding compositions wherein the silica abrasive exhibits a pH of 3.5-4.5 in an aqueous slurry of the abrasive.
1.04 Any of the preceding compositions wherein the silica abrasive which exhibits an acid pH when measured as an aqueous slurry is present in an amount from 2 to 35 weight percent.
1.05 Any of the preceding compositions wherein the silica abrasive which exhibits an acid pH when measured as an aqueous slurry is present in an amount from 3 to 15 weight percent.
1.06 Any of the preceding compositions wherein the silica abrasive which exhibits an acid pH when measured as an aqueous slurry is present in an amount selected from 2 wt. %, 3 wt. %, 4% wt. %, 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %.
1.07 Any of the preceding compositions wherein the basic amino acid has the L-configuration (e.g., L-arginine).
1.08 Any of the preceding compositions wherein the basic amino acid is arginine or lysine is in free form.
1.09 Any of the preceding compositions wherein the basic amino acid is provided in the form of a di- or tri-peptide comprising arginine or lysine, or salts thereof.
1.10 Any of the preceding compositions wherein the basic amino acid is arginine or lysine, and wherein the arginine or lysine is present in an amount corresponding to 1% to 15%, e.g., 3 wt. % to 10 wt. % of the total composition weight, about e.g., 1.5%, 4%, 5%, or 8%, wherein the weight of the basic amino acid is calculated as free form.
1.11 Any of the preceding compositions wherein the amino acid is arginine from 0.1 wt. %-6.0 wt. %. (e.g., about 1.5 wt %).
1.12 Any of the preceding compositions wherein the amino acid is arginine from about 1.5 wt. %.
1.13 Any of the preceding compositions wherein the amino acid is arginine from 4.5 wt. %-8.5 wt. % (e.g., 5.0%).
1.14 Any of the preceding compositions wherein the amino acid is arginine from about 5.0 wt. %.
1.15 Any of the preceding compositions wherein the amino acid is arginine from 3.5 wt. %-9 wt. %.
1.16 Any of the preceding compositions wherein the amino acid is arginine from about 8.0 wt. %.
1.17 Any of the preceding compositions wherein the amino acid is L-arginine.
1.18 Any of the preceding compositions wherein the amino acid is a free form arginine.
1.19 Any of the preceding compositions wherein the basic amino acid is lysine (e.g., 2% wt., 3% wt., 4% wt., 5% wt., 6% wt.), (e.g., 4% wt.).
1.20 Any of the preceding compositions wherein the amino acid is lysine from 1.0 wt. %-6.0 wt. %.
1.21 Any of the preceding compositions wherein the amino acid is lysine from about 1.5 wt. %.
1.22 Any of the preceding compositions wherein the amino acid is lysine from about 4.0 wt. %.
1.23 Any of the preceding compositions wherein the amino acid is L-lysine.
1.24 Any of the preceding compositions wherein the amino acid is free form lysine.

1.25 Any of the preceding compositions wherein the amino acid is arginine or lysine in partially or wholly in salt form.
1.26 Composition 1.25 wherein the amino acid is arginine phosphate.
1.27 Composition 1.25 wherein the amino acid is arginine hydrochloride.
1.28 Composition 1.25 wherein the amino acid is arginine bicarbonate.
1.29 Composition 1.25 wherein the amino acid is lysine phosphate.
1.30 Composition 1.25 wherein the amino acid is lysine hydrochloride.
1.31 Composition 1.25 wherein the amino acid is lysine bicarbonate.
1.32 Any of the preceding compositions wherein the amino acid is arginine or lysine ionized by neutralization with an acid or a salt of an acid.
1.33 Any of preceding compositions wherein the composition is ethanol-free.
1.34 Any of the preceding compositions further comprising a fluoride source selected from: stannous fluoride, sodium fluoride, potassium fluoride, sodium monofluorophosphate, sodium fluorosilicate, ammonium fluorosilicate, amine fluoride (e.g., N'-octadecyltrimethylendiamine-N, N,N'-tris(2-ethanol)-dihydrofluoride), ammonium fluoride, titanium fluoride, hexafluorosulfate, and combinations thereof.
1.35 The composition of 1.34, wherein the fluoride source is stannous fluoride.
1.36 Any of the preceding compositions wherein the fluoride source is a fluorophosphate.
1.37 Any of the preceding compositions wherein the fluoride source is sodium monofluorophosphate.
1.38 The composition of 1.34, wherein the fluoride source is sodium fluoride.
1.39 Any of the preceding compositions wherein the fluoride source is a fluoride salt present in an amount of 0.1 wt. % to 2 wt. % (0.1 wt %-0.6 wt. %) of the total composition weight (e.g., sodium fluoride (e.g., about 0.32 wt. %) or sodium monofluorophosphate).
1.40 Any of the preceding compositions wherein the fluoride source is sodium fluoride in an amount about 0.32 wt. % based on the weight of the composition.
1.41 Any of the preceding compositions wherein the fluoride source is a soluble fluoride salt which provides fluoride ion in an amount of from 50 to 25,000 ppm (e.g., 750-2000 ppm, e.g., 1000-1500 ppm, e.g., about 1000 ppm, e.g., about 1450 ppm)
1.42 Any of the preceding compositions wherein the fluoride source is sodium fluoride which provides fluoride in an amount from 750-2000 ppm (e.g., about 1450 ppm).
1.43 Any of the preceding compositions wherein the fluoride source is selected from sodium fluoride and sodium monofluorophosphate and which provides fluoride in an amount from 1000 ppm-1500 ppm.
1.44 Any of the preceding compositions wherein the fluoride source is sodium fluoride or sodium monofluorophosphate and which provides fluoride in an amount of about 1450 ppm.
1.45 Any of the preceding compositions wherein the pH is between 6.0 and 10.5, e.g., 7.0 to 9.0, e.g., about 8.0.
1.46 Any of the preceding compositions further comprising calcium carbonate.
1.47 The composition of 1.46, wherein the calcium carbonate is a precipitated calcium carbonate high absorption (e.g., 20% to 30% by weight of the composition) (e.g., 25% precipitated calcium carbonate high absorption).
1.48 The composition of 1.47, further comprising a precipitated calcium carbonate—light (e.g., about 10% precipitated calcium carbonate—light) (e.g., about 10% natural calcium carbonate).
1.49 Any of the preceding compositions further comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, disodium hydrogenorthophosphate, monosodium phosphate, pentapotassium triphosphate and mixtures of any of two or more of these, in an amount of 0.1-20%, e.g., 0.1-8%, e.g., e.g., 0.2 to 5%, e.g., 0.3 to 2%, e.g., 0.3 to 1%, e.g about 0.5%, about 1%, about 2%, about 5%, about 6%, by weight of the composition.
1.50 Any of the preceding compositions comprising tetrapotassium pyrophosphate, disodium hydrogenorthophosphate, monosodium phosphate, and pentapotassium triphosphate.
1.51 Any of the preceding compositions, wherein the composition further comprises stannous pyrophosphate, wherein the stannous pyrophosphate is from 0.1%-3% by wt. of the composition. (e.g., about 1% by wt. of the composition).
1.52 Any of the preceding compositions comprising a polyphosphate.
1.53 The composition of 1.49, wherein the polyphosphate is tetrasodium pyrophosphate.
1.54 The composition of 1.53, wherein the tetrasodium pyrophosphate is from 0.1-1.0 wt % (e.g., about 0.5 wt %).
1.55 Any of the preceding compositions further comprising a second abrasive or particulate (e.g., silica).
1.56 Any of the preceding compositions wherein the second abrasive silica is synthetic amorphous silica. (e.g., 1%-28% by wt.) (e.g., 8%-25% by wt.)
1.57 Any of the preceding composition wherein the silica abrasives are silica gels or precipitated amorphous silicas, e.g. silicas having an average particle size ranging from 2.5 microns to 12 microns.
1.58 Any of the preceding compositions further comprising a small particle silica having a median particle size (d50) of 1-5 microns (e.g., 3-4 microns) (e.g., about 5 wt. % Sorbosil AC43 from PQ Chemicals, Warrington, United Kingdom).
1.59 Any of the preceding compositions wherein 20-30 wt % of the total silica in the composition is small particle silica (e.g., having a median particle size (d50) of 3-4 microns) and wherein the small particle silica is about 5 wt. % of the oral care composition.
1.60 Any of the preceding compositions comprising silica wherein the silica is used as a thickening agent, e.g., particle silica.
1.61 Any of the preceding compositions further comprising a nonionic surfactant, wherein the nonionic surfactant is in an amount of from 0.5-5%, e.g, 1-2%, selected from poloxamers (e.g., poloxamer 407), polysorbates (e.g., polysorbate 20), polyoxyl hydrogenated castor oil (e.g., polyoxyl 40 hydrogenated castor oil), and mixtures thereof.

1.62 Any of the preceding compositions, wherein the poloxamer nonionic surfactant has an average polyoxypropylene molecular mass (Mw) of from 3000 to 5000 g/mol and a polyoxyethylene content of from 60 to 80 mol %, e.g., the poloxamer nonionic surfactant comprises poloxamer 407.

1.63 Any of the preceding compositions further comprising glycerin, wherein the glycerin is in a total amount of 25-40% (e.g., about 35%).

1.64 The composition of 1.63, wherein the glycerin is in an amount of about 35% by wt. of the composition.

1.65 The composition of 1.63, wherein the glycerin is in an amount of about 26% by wt. of the composition.

1.66 Any of the preceding compositions further comprising sorbitol, wherein the sorbitol is in a total amount of 10-40% (e.g., about 23%).

1.67 The composition of 1.66, wherein the sorbitol is in an amount of about 13% by wt. of the composition.

1.68 The composition of any of 1.63-1.67, wherein the glycerin is an amount of about 26% by wt., and the sorbitol is in an amount of about 13% by wt.

1.69 Any of the preceding compositions, wherein the ratio of the amount of zinc oxide (e.g., wt. %) to zinc citrate (e.g., wt %) is from 1.5:1 to 4.5:1 (e.g., 2:1, 2.5:1, 3:1, 3.5:1, or 4:1).

1.70 Any of the preceding compositions, wherein the zinc citrate is in an amount of from 0.25 to 1.0 wt % (e.g., 0.5 wt. %) and zinc oxide may be present in an amount of from 0.75 to 1.25 wt % (e.g., 1.0 wt. %) based on the weight of the oral care composition.

1.71 Any of the preceding compositions wherein the zinc citrate is about 0.5 wt %.

1.72 Any of the preceding compositions wherein the zinc oxide is about 1.0 wt %.

1.73 Any of the preceding compositions where the zinc citrate is about 0.5 wt % and the zinc oxide is about 1.0 wt %.

1.74 Any of the preceding compositions further comprising an additional ingredient selected from: benzyl alcohol, Methylisothizolinone ("MIT"), Sodium bicarbonate, sodium methyl cocoyl taurate (tauranol), lauryl alcohol, and polyphosphate.

1.75 Any of the preceding compositions wherein the benzyl alcohol is present from 0.1-0.6 wt %., (e.g., 0.1-0.4 wt %) e.g. about 0.1 wt. %, about 0.2 wt. %, or about 0.3 wt. %.

1.76 Any of the preceding compositions wherein the benzyl alcohol is about 0.1 wt %.

1.77 Any of the preceding compositions wherein the benzyl alcohol is considered a preservative.

1.78 Any of the preceding compositions comprising polymer films.

1.79 Any of the preceding compositions comprising flavoring, fragrance and/or coloring.

1.80 The composition of 1.65, wherein the flavoring agent is sodium saccharin, sucralose, or a mixture thereof 1.81 Any of the preceding compositions, wherein the composition comprises a thickening agents selected from the group consisting of carboxyvinyl polymers, xanthan gum, carrageenan, hydroxyethyl cellulose and water soluble salts of cellulose ethers (e.g., sodium carboxymethyl cellulose and sodium carboxymethyl hydroxyethyl cellulose).

1.82 Any of the preceding compositions, wherein the compositions comprises sodium carboxymethyl cellulose (e.g., from 0.5 wt. %-1.5 wt. %).

1.83 Any of the preceding compositions comprising from 5%-40%, e.g., 10%-35%, e.g., about 15%, 25%, 30%, and 35% water.

1.84 Any of the preceding compositions comprising an additional antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, honokiol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts and zinc compounds, for example, Zinc Chloride, Zinc Lactate, Zinc Sulfate, Zinc Oxide, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.

1.85 Any of the preceding compositions comprising an antioxidant, e.g., selected from the group consisting of Co-enzyme Q10, PQQ, Vitamin C, Vitamin E, Vitamin A, BHT, anethole-dithiothione, and mixtures thereof 1.86 Any of the preceding compositions comprising a whitening agent.

1.87 Any of the preceding compositions comprising a whitening agent selected from a whitening active selected from the group consisting of peroxides, metal chlorites, perborates, percarbonates, peroxyacids, hypochlorites, and combinations thereof.

1.88 Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.

1.89 Any of the preceding compositions further comprising an agent that interferes with or prevents bacterial attachment, e.g., ethyl lauryl arginate (ELA) or chitosan.

1.90 Any of the preceding compositions comprising:
 a. about 1.0% zinc oxide
 b. about 0.5% zinc citrate
 c. about 1.5% L-arginine
 d. about 0.32% sodium fluoride;
 e. about 3 wt. % to 15 wt. % silica abrasive which exhibits an acid pH when measured as an aqueous slurry (e.g., prophy silica) (e.g., Sylodent 783)

1.91 Any of the preceding compositions comprising:
 a. about 1.0% zinc oxide
 b. about 0.5% zinc citrate
 c. about 5% L-arginine
 d. about 0.32% sodium fluoride
 e. about 10 wt. % to 15 wt. % silica abrasive which exhibits an acid pH when measured as an aqueous slurry (e.g., prophy silica) (e.g., Sylodent 783), and 1.92 Any of the preceding compositions comprising:
   a. about 1.0% zinc oxide
   b. about 0.5% zinc citrate
   c. about 5% L-arginine
   d. about 0.32% sodium fluoride;
   e. about 3 wt. % to 15 wt. % silica abrasive which exhibits an acid pH when measured as an aqueous slurry. (e.g., prophy silica) (e.g., Sylodent 783)
1.93 Any of the preceding compositions comprising a silica, wherein the silica is Zeodent 114.
1.94 Any of the preceding compositions effective upon application to the oral cavity, e.g., by rinsing, optionally in conjunction with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) treat, relieve or reduce dry mouth, (xiii) clean the teeth and oral cavity (xiv) reduce erosion, (xv) prevents stains and/or whiten teeth, (xvi) immunize the teeth against cariogenic bacteria; and/or (xvii) promote systemic health, including cardiovascular health, e.g., by reducing potential for systemic infection via the oral tissues.
1.95 Any of the preceding oral compositions, wherein the oral composition may be any of the following oral compositions selected from the group consisting of: a toothpaste or a dentifrice, a mouthwash or a mouth rinse, a topical oral gel, and a denture cleanser.
1.96 A composition obtained or obtainable by combining the ingredients as set forth in any of the preceding compositions.
1.97 A composition obtained or obtainable by combining the ingredients as set forth in any of the preceding compositions.
1.98 A composition for use as set for in any of the preceding compositions.

In another embodiment, the invention encompasses a method to improve oral health comprising applying an effective amount of the oral composition of any of the embodiments set forth above (e.g., any of Composition 1.0 et seq) to the oral cavity of a subject in need thereof, e.g.,
   i. a method to reduce or inhibit formation of dental caries, reduce, repair or inhibit early enamel lesions, e.g., as detected by quantitative light-induced fluorescence (QLF) or electrical caries measurement (ECM),
   ii. reduce or inhibit demineralization and promote remineralization of the teeth,
   iii. reduce hypersensitivity of the teeth,
   iv. reduce or inhibit gingivitis,
   v. promote healing of sores or cuts in the mouth,
   vi. reduce levels of acid producing bacteria,
   vii. to increase relative levels of arginolytic bacteria,
   viii. inhibit microbial bio film formation in the oral cavity,
   ix. raise and/or maintain plaque pH at levels of at least pH 5.5 following sugar challenge,
   x. reduce plaque accumulation,
   xi. treat dry mouth,
   xii. enhance systemic health, including cardiovascular health, e.g., by reducing potential for systemic infection via the oral tissues,
   xiii. Whiten teeth,
   xiv. reduce erosion of the teeth,
   xv. immunize (or protect) the teeth against cariogenic bacteria and their effects, and/or
   xvi. clean the teeth and oral cavity.

The invention further comprises the use of sodium bicarbonate, sodium methyl cocoyl taurate (tauranol), methylisothiazolinone, and benzyl alcohol and combinations thereof in the manufacture of a Composition of the Invention, e.g., for use in any of the indications set forth in the above method of Composition 1.0, et seq.

DETAILED DESCRIPTION

As used herein, the term "oral composition" means the total composition that is delivered to the oral surfaces. The composition is further defined as a product which, during the normal course of usage, is not, the purposes of systemic administration of particular therapeutic agents, intentionally swallowed but is rather retained in the oral cavity for a time sufficient to contact substantially all of the dental surfaces and/or oral tissues for the purposes of oral activity. Examples of such compositions include, but are not limited to, toothpaste or a dentifrice, a mouthwash or a mouth rinse, a topical oral gel, a denture cleanser, and the like.

As used herein, the term "dentifrice" means paste, gel, or liquid formulations unless otherwise specified. The dentifrice composition can be in any desired form such as deep striped, surface striped, multi-layered, having the gel surrounding the paste, or any combination thereof. Alternatively the oral composition is provided as a dual phase composition, wherein individual compositions are combined when dispensed from a separated compartment dispenser.

Basic Amino Acids

The basic amino acids which can be used in the compositions and methods of the invention include not only naturally occurring basic amino acids, such as arginine, lysine, and histidine, but also any basic amino acids having a carboxyl group and an amino group in the molecule, which are water-soluble and provide an aqueous solution with a pH of 7 or greater.

Accordingly, basic amino acids include, but are not limited to, arginine, lysine, serine, citrullene, ornithine, creatine, histidine, diaminobutanoic acid, diaminoproprionic acid, salts thereof or combinations thereof. In a particular embodiment, the basic amino acids are selected from arginine, citrullene, and ornithine.

In certain embodiments, the basic amino acid is arginine, for example, L-arginine, or a salt thereof.

The compositions of the invention are intended for topical use in the mouth and so salts for use in the present invention should be safe for such use, in the amounts and concentrations provided. Suitable salts include salts known in the art to be pharmaceutically acceptable salts which are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

Fluoride Ion Source

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., each of which are incorporated herein by reference. Representative fluoride ion sources used with the present invention (e.g., Composition 1.0 et seq.) include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. Where the formulation comprises calcium salts, the fluoride salts are preferably salts wherein the fluoride is covalently bound to another atom, e.g., as in sodium monofluorophosphate, rather than merely ionically bound, e.g., as in sodium fluoride.

Surfactants

The invention may in some embodiments contain anionic surfactants, e.g., the Compositions of Composition 1.0, et seq., for example, water-soluble salts of higher fatty acid monoglyceride monosulfates, such as the sodium salt of the monosulfated monoglyceride of hydrogenated coconut oil fatty acids such as sodium N-methyl N-cocoyl taurate, sodium coco-glyceride sulfate; higher alkyl sulfates, such as sodium lauryl sulfate; higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or, for example sodium laureth-2 sulfate ($CH_3(CH2)_{10}CH_2(OCH_2CH_2)_2OSO_3Na$); higher alkyl aryl sulfonates such as sodium dodecyl benzene sulfonate (sodium lauryl benzene sulfonate); higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. By "higher alkyl" is meant, e.g., $C_{6-3}0$ alkyl. In particular embodiments, the anionic surfactant (where present) is selected from sodium lauryl sulfate and sodium ether lauryl sulfate. When present, the anionic surfactant is present in an amount which is effective, e.g., >0.001% by weight of the formulation, but not at a concentration which would be irritating to the oral tissue, e.g., 1%, and optimal concentrations depend on the particular formulation and the particular surfactant. In one embodiment, the anionic surfactant is present at from 0.03% to 5% by weight, e.g., 1.5%.

Cationic surfactants useful in the present invention can be broadly defined as derivatives of aliphatic quaternary ammonium compounds having one long alkyl chain containing 8 to 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof. Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants of Composition 1.0, et seq., that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. In a particular embodiment, the composition of the invention comprises a nonionic surfactant selected from polaxamers (e.g., polaxamer 407), polysorbates (e.g., polysorbate 20), polyoxyl hydrogenated castor oils (e.g., polyoxyl 40 hydrogenated castor oil), and mixtures thereof.

Illustrative amphoteric surfactants of Composition 1.0, et seq., that can be used in the compositions of the invention include betaines (such as cocamidopropylbetaine), derivatives of aliphatic secondary and tertiary amines in which the aliphatic radical can be a straight or branched chain and wherein one of the aliphatic substituents contains about 8-18 carbon atoms and one contains an anionic water-solubilizing group (such as carboxylate, sulfonate, sulfate, phosphate or phosphonate), and mixtures of such materials.

Illustrative zwitterionic surfactants of Composition 1.0, et seq., that can be used in the compositions of the invention include derivatives of aliphatic quaternary ammonium, phosphonium and sulfonium compounds in which the aliphatic radical can be a straight or branched chain and wherein one of the aliphatic substituents contains about 8-18 carbon atoms and one contains an anionic water-solubilizing group (such as carboxy, sulfonate, sulfate, phosphate or phosphonate). The surfactant or mixtures of compatible surfactants can be present in the compositions of the present invention in 0.1% to 5%, in another embodiment 0.3% to 3% and in another embodiment 0.5% to 2% by weight of the total composition.

Flavoring Agents

The oral care compositions of the invention may also include a flavoring agent. Flavoring agents which are used in the practice of the present invention include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

The flavoring agent is incorporated in the oral composition at a concentration of 0.01 to 1% by weight.

Chelating and Anti-Calculus Agents

The oral care compositions of the invention (e.g., Composition 1.0 et seq) also may include one or more chelating agents able to complex calcium found in the cell walls of the bacteria. Binding of this calcium weakens the bacterial cell wall and augments bacterial lysis.

Another group of agents suitable for use as chelating or anti-calculus agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide least 0.1 wt. % pyrophosphate ions, e.g., 0.1 to 3 wt 5, e.g., 0.1 to 2 wt %, e.g., 0.1 to 1 wt %, e.g., 0.2 to 0.5 wt %. The pyrophosphates also contribute to preservation of the compositions by lowering the effect of water activity.

Polymers

The oral care compositions of the invention (e.g., Composition 1.0, et seq) also optionally include one or more polymers, such as polyethylene glycols, polyvinyl methyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Certain embodiments include 1:4 to 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000. These copolymers are available for example as Gantrez AN 139 (M.W. 500,000), AN 1 19 (M.W. 250,000) and S-97 Pharmaceutical Grade (M.W. 70,000), of GAF Chemicals Corporation.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1 103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorosorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, xanthan gum, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

Abrasives

Generally, the inclusion of abrasives in dentifrice formulations is necessary for effective cleaning of teeth by brushing. It has been determined that by including an abrasive silica having an acid pH in the composition, compositions of enhanced viscosity stability are obtained. Prophy silica available from Grace, offered as Sylodent™, can be used with various embodiments of the present invention (e.g., Composition 1.0 et seq).

The acidic silica abrasive is included in the dentifrice components at a concentration of about 2 to about 35% by weight; about 3 to about 20% by weight, about 3 to about 15% by weight, about 10 to about 15% by weight. For example, the acidic silica abrasive may be present in an amount selected from 2 wt. %, 3 wt. %, 4% wt. %, 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %.

A commercially available acidic silica abrasive is Sylodent 783 available from W. R. Grace & Company, Baltimore, Md. Sylodent 783 has a pH of 3.4-4.2 when measured as a 5% by weight slurry in water. For use in the present invention, the silica material has an average particle size of less than 10 microns, e.g., 3-7 microns, e.g. about 5.5 microns. For example a small particle silica may have an average particle size (D50) of 2.5-4.5 microns.

The composition may also include any silica suitable for oral care compositions, such as precipitated silicas or silica gels. For example synthetic amorphous silica. Silica may also be available as a thickening agent, e.g., particle silica. For example, the silica can also be small particle silica (e.g., Sorbosil AC43 from PQ Corporation, Warrington, United Kingdom). However the additional abrasives are preferably not present in a type or amount so as to increase the RDA of the dentifrice to levels which could damage sensitive teeth, e.g., greater than 130.

The invention may also comprise a commercially available cleaning silica in certain embodiments of the invention (e.g., any of Composition 1.0, et seq). Zeodent 114 offered by J. M. Huber Finland Oy Telakkatie 5 FIN-49460 Hamina, is one such commercially available silica.

Water

Water is present in the oral compositions of the invention. Water, employed in the preparation of commercial oral compositions should be deionized and free of organic impurities. Water commonly makes up the balance of the compositions and includes 5% to 45%, e.g., 10% to 20%, e.g., 25-35%, by weight of the oral compositions. This amount of water includes the free water which is added plus that amount which is introduced with other materials such as with sorbitol or silica or any components of the invention. The Karl Fischer method is a one measure of calculating free water.

Humectants

Within certain embodiments of the oral compositions (e.g., Composition 1.0 et seq), it is also desirable to incorporate a humectant to reduce evaporation and also contribute towards preservation by lowering water activity. Certain humectants can also impart desirable sweetness or flavor to the compositions. The humectant, on a pure humectant basis, generally includes 15% to 70% in one embodiment or 30% to 65% in another embodiment by weight of the composition.

Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the compositions herein.

The present invention in its method aspect involves applying to the oral cavity a safe and effective amount of the compositions described herein.

The compositions and methods according to the invention (e.g., Composition 1.0 et seq) can be incorporated into oral compositions for the care of the mouth and teeth such as toothpastes, transparent pastes, gels, mouth rinses, sprays and chewing gum.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Example 1

The examples herein detail how the viscosity over time for a composition which exhibits a problem of rapid reduction in viscosity (Run A), is compared to five compositions which show the stabilized viscosity provided by the invention (Compositions 1-5 in Table 1).

Viscosity is measured on a Brookfield HADV2 viscometer using a V74 vane spindle. This viscometer applies a user-controlled angular velocity to the spindle, typically measured in rotations per second (RPM), and reports torque on the shaft of the spindle. Viscosity is then calculated from RPM and torque as explained in the Brookfield Manual (Operating Instructions) using too conversion parameters SRC (shear rate constant) and SMC (spindle multiplier constant). The conversion parameters are defined as follows: SMC=290, SRC=0.2723. The test is performed at room temperature, and varies between 22 and 25 deg. C. During the test, RPM of the spindle is swept from 200 to 0.5 in 12 steps, 10 seconds per step. The viscosity reading reported is taken at RPM=1.

Compositions containing zinc oxide, zinc citrate, arginine and a fluoride source are prepared as described in Table 1, below. All compositions are formulated to provide a 10% pH of 8-8.5 using 0-0.35% phosphoric acid. The composition identified as Run A does not contain a silica abrasive which exhibits an acid pH when measured as an aqueous slurry. The compositions identified as Compositions 1-5 in Table 1 contain a silica abrasive which exhibits an acid pH (Prophy Silica—Sylodent 783) when measured as an aqueous slurry in varying amounts, as detailed below.

TABLE 1

Dentifrice Formulations

| INGREDIENTS | Experiment ID | | | | | |
|---|---|---|---|---|---|---|
| | Run A | Composition 1 | Composition 2 | Composition 3 | Composition 4 | Composition 5 |
| 99.0%-101.0% GLYCERIN - USP, EP VEG | 35 | 35 | 35 | 35 | 35 | 35 |
| DEMINERALIZED WATER | Q.S. | Q.S. | Q.S. | Q.S. | Q.S. | Q.S. |
| PROPHY SILICA (SYLODENT 783) | 0 | 15 | 10 | 5 | 5 | 3 |
| ABRASIVES (e.g., includes Abrasive silcas, High Cleaning Silicas) | 20 | 5 | 10 | 15 | 15 | 17 |
| SILICA-THICKENER | 6.5 | 7 | 7 | 7 | 7 | 7 |
| ANIONIC SURFACTANT | 2 | 2 | 2 | 2 | 2 | 2 |
| L-ARGININE | 1.5 | 1.5 | 1.5 | 1.5 | 1.5 | 1.5 |
| AMPHOTERIC SURFACTANT | 1.25 | 1.25 | 1.25 | 1.25 | 1.25 | 1.25 |
| NON-IONIC SURFACTANT | 0.75 | 0.75 | 0.75 | 0.75 | 0.75 | 0.75 |
| ZINC OXIDE | 1 | 1 | 1 | 1 | 1 | 1 |

TABLE 1-continued

Dentifrice Formulations

| INGREDIENTS | Run A | Composition 1 | Composition 2 | Composition 3 | Composition 4 | Composition 5 |
|---|---|---|---|---|---|---|
| POLYMER | 1 | 1.3 | 1.3 | 1.3 | 1.3 | 1.3 |
| COLORANT | 0.75 | 0.75 | 0.75 | 0.75 | 0.75 | 0.75 |
| ALKALI PHOSPHATE SALT | 0.5 | 0.5 | 0.5 | 0.5 | 0.5 | 0.5 |
| ZINC CITRATE TRIHYDRATE | 0.5 | 0.5 | 0.5 | 0.5 | 0.5 | 0.5 |
| PRESERVATIVE | 0.4 | 0.4 | 0.4 | 0.4 | 0.4 | 0.4 |
| SODIUM FLUORIDE - USP, EP | 0.32 | 0.32 | 0.32 | 0.32 | 0.32 | 0.32 |
| 85% SYRUPY PHOSPHORIC ACID - FOOD GRADE | 0.35 | 0 | 0 | 0 | 0 | 0 |
| FLAVORING AGENT | 2 | 2 | 2 | 2 | 1.82 | 1.52 |
| TOTAL COMPONENTS | 100 | 100 | 100 | 100 | 100 | 100 |

The composition identified as Run A displays an initial viscosity which is initially 500,000 cps to 600,000 cps high, but decreases to under 400,000 cps in 2 weeks, and under 200,000 cps at 6 weeks. Surprisingly, the compositions containing a silica abrasive which exhibits an acid pH (Prophy Silica—Sylodent 783) when measured as an aqueous slurry, Compositions 1 to 5 in Table 1, eliminate this undesirable characteristic and instead produce viscosities that are stable or increase over time (See, Table 2).

TABLE 2

Viscosity data.

| Time | Run A | Composition 1 | Composition 2 | Composition 3 | Composition 4 | Composition 5 |
|---|---|---|---|---|---|---|
| | | | Viscosity (cps) | | | |
| 0 | z | | | | 491040 | 363489 |
| 1 d | 539119 | 211912 | 300155 | 272475 | | |
| 5 d | 601597 | | | 309816 | | |
| 1 wk | 627362 | | 288561 | | 383245 | 371651 |
| 2 wk | 433485 | 340733 | | 328495 | 403212 | 364565 |
| 3 wk | | 343310 | 314325 | 334292 | | |
| 4 wk | 224794 | 395483 | 304019 | | 430909 | 423823 |
| 5 wk | | 375515 | 338801 | 322698 | | |
| 6 wk | 193233 | 376804 | 344598 | 334292 | 406432 | 442503 |
| 7 wk | | | 334292 | | | |
| 9 wk | | | 387753 | | | |
| 10 wk | | 351039 | | 364565 | | |
| 11 wk | 158451 | | 373583 | 381956 | | |
| 12 wk | | 405788 | 357480 | | | |
| 13 wk | | 405788 | 398059 | 393550 | | |

Upon further investigation, it was found that the silica abrasive which exhibits an acid pH when measured as an aqueous slurry silica is acidic (pH 3.4-4.2) does not require phosphoric acid to adjust the product pH. Other abrasive silicas and high cleaning silicas are about neutral in pH (pH 7-8) and thus, require phosphoric acid for pH adjustment.

TABLE 3

Viscosity Data

| | Composition 6 | Composition 7 | Composition 8 |
|---|---|---|---|
| Demineralized Water | Q.S. | Q.S. | Q.S. |
| Glycerin - 99.5% | 35 | 35 | 35 |

TABLE 3-continued

Viscosity Data

| | Composition 6 | Composition 7 | Composition 8 |
|---|---|---|---|
| Polymer | 1.2 | 1.2 | 1.2 |
| Zinc Oxide | 1 | 1 | 1 |
| Zinc Citrate | 0.5 | 0.5 | 0.5 |
| Alkali Phosphate Salt | 0.5 | 0.5 | 0.5 |
| Flavoring agent | 1.82 | 1.82 | 1.82 |
| Sodium Fluoride | 0.32 | 0.32 | 0.32 |
| Colorant | 0.75 | 0.75 | 0.75 |
| L-Arginine | 1.5 | 1.5 | 1.5 |
| Non-Ionic Surfactant | 0.5 | 0.5 | 0.5 |
| Abrasives | 8 | 10 | 12 |

TABLE 3-continued

Viscosity Data

|  | Composition 6 | Composition 7 | Composition 8 |
|---|---|---|---|
| (e.g., includes Abrasive Silcas, High Cleaning Silicas) | | | |
| Prophy silica (Sylodent 783) | 7 | 5 | 3 |
| Silica - thickener | 7 | 7 | 8.5 |
| Preservative | 0.4 | 0.4 | 0.4 |
| Anionic Surfactant | 5.7 | 5.7 | 5.7 |
| Amphoteric Surfactant | 1.25 | 1.25 | 1.25 |
| Total Components | 100 | 100 | 100 |

Upon further investigation, when phosphoric acid is removed from further formulations (Compositions 6-8 in Table 3), they demonstrate improvement in viscosity stability, and this viscosity trend remained relatively stable from day 1 to 4 weeks when tested at: room temperature, 40° C., and 49° C. The data is further detailed in Table 4 below.

TABLE 4

| | Composition 6 Viscosity, $10^3$ cps | | | Composition 7 Viscosity, $10^3$ cps | | | Composion 8 Viscosity, $10^3$ cps | | |
|---|---|---|---|---|---|---|---|---|---|
| | RT | 40 C. | 49 C. | RT | 40 C. | 49 C. | RT | 40 C. | 49 C. |
| 0 | 471 | | | 324 | | | 336 | | |
| 0.14 | 370 | | | 197 | | | 268 | | |
| 1 | 363 | 418 | 390 | 200 | 227 | 258 | 230 | 256 | 263 |
| 2 | 360 | 430 | 440 | 201 | 243 | 269 | 220 | 250 | 258 |
| 3 | 325 | | | 205 | 246 | 245 | 228 | 277 | 274 |
| 4 | 314 | 412 | 385 | 224 | 253 | 253 | 227 | 268 | 272 |
| 6 | 327 | | | 218 | | | 233 | | |

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

While the present invention has been described with reference to embodiments, it will be understood by those skilled in the art that various modifications and variations may be made therein without departing from the scope of the present invention as defined by the appended claims.

The invention claimed is:

1. An oral care composition comprising:
   a. a basic amino acid in free or salt form wherein the amino acid is arginine;
   b. zinc oxide and zinc citrate;
   c. a fluoride source; and
   d. a silica abrasive which exhibits a pH of 3.5-4.5 when measured as an aqueous slurry; wherein said silica abrasive is present in an amount of about 3 wt. % to about 15 wt. % based on the total weight of the composition; and
   wherein the oral care composition increases viscosity over 2-13 weeks after aging, or does not drop more than 18% in viscosity over 2-13 weeks of ageing, wherein the aging is measured from day 1.

2. The oral care composition of claim 1, wherein the arginine has a L-configuration; and wherein the arginine is present in an amount corresponding to 1% to 15% based on the total weight of the composition, the weight of the arginine being calculated as free form.

3. The oral care composition of claim 1 wherein the arginine is present in the amount of about 1.5 wt. %, 5.0 wt. % or 8.0 wt. % based on the total weight of the composition.

4. The oral care composition of claim 1, wherein the amino acid is arginine in free form.

5. The oral care composition of claim 1, wherein the ratio of the amount of zinc oxide to zinc citrate is 2:1, 2.5:1, 3:1, 3.5:1 or 4:1, wherein the ratio is by wt. of the overall composition.

6. The oral care composition of claim 1, wherein the zinc citrate is in an amount of from 0.25 to 1.0 wt % and zinc oxide is present in an amount of from 0.75 to 1.25 wt % based on the total weight of the oral care composition.

7. The oral care composition of claim 1, wherein the zinc citrate is in an amount of about 0.5 wt % and zinc oxide is present in an amount of about 1.0% based on the total weight of the oral care composition.

8. The oral care composition of claim 1, wherein the fluoride source is sodium fluoride or sodium monofluorophosphate.

9. The oral care composition of claim 8, wherein the sodium fluoride or sodium monofluorophosphate is from 0.1 wt. %-2 wt. % of the total composition weight.

10. The composition of claim 1, wherein the fluoride source is stannous fluoride.

11. The oral care composition of claim 1, further comprising an additional ingredient selected from: benzyl alcohol, methylisothizolinone (MIT), sodium bicarbonate, sodium methyl cocoyl taurate, lauryl alcohol, and polyphosphate.

12. The oral care composition of claim 11, wherein the additional ingredient is benzyl alcohol, and wherein the benzyl alcohol is present from 0.1-0.6% wt., based on the total weight of the composition.

13. The oral care composition of claim 1, comprising:
   a. about 1.0% zinc oxide
   b. about 0.5% zinc citrate
   c. about 1.5% L-arginine
   d. about 0.32% sodium fluoride; and
   e. about 3 wt. % to 15 wt. % silica abrasive which exhibits an acid pH when measured as an aqueous slurry; wherein the amounts are based on the total weight of the composition; and wherein the oral care composition increases viscosity over 2-13 weeks after aging, or does not drop more than 18% in viscosity over 2-13 weeks of ageing, wherein the aging is measured from day 1.

14. The oral care composition of claim 1, comprising:
   a. about 1.0% zinc oxide
   b. about 0.5% zinc citrate
   c. about 5% L-arginine
   d. about 0.32% sodium fluoride; and
   e. about 10 wt. % to 15 wt. % silica abrasive which exhibits an acid pH when measured as an aqueous slurry;
   wherein the amounts are based on the total weight of the composition and wherein the oral care composition increases viscosity over 2-13 weeks after aging, or does not drop more than 18% in viscosity over 2-13 weeks of ageing, wherein the aging is measured from day 1.

15. The oral care composition of claim 1, wherein the oral composition is selected from the group consisting of: a toothpaste or a dentifrice, a mouthwash or a mouth rinse, a topical oral gel, and a denture cleanser.

16. The oral care composition of claim 1, wherein the composition has a viscosity at four (4) weeks of from 30,000 cps-44,000 cps as measured by a Brookfield HADV2 viscometer.

17. A method to improve oral health comprising applying an effective amount of the oral composition of claim 1, to the oral cavity of a subject in need thereof, wherein the method is effective to:
   i. reduce or inhibit formation of dental caries,
   ii. reduce, repair or inhibit early enamel lesions,
   iii. reduce or inhibit demineralization and promote remineralization of the teeth,
   iv. reduce hypersensitivity of the teeth,
   v. reduce or inhibit gingivitis,
   vi. promote healing of sores or cuts in the mouth,
   vii. reduce levels of acid producing bacteria,
   viii. increase relative levels of arginolytic bacteria,
   ix. inhibit microbial bio film formation in the oral cavity,
   x. raise and/or maintain plaque pH at levels of at least pH 5.5 following sugar challenge,
   xi. reduce plaque accumulation,
   xii. treat dry mouth,
   xiii. enhance systemic health,
   xiv. whiten teeth,
   xv. reduce erosion of the teeth,
   xvi. immunize the teeth against cariogenic bacteria and their effects, and/or
   xvii. clean the teeth and oral cavity.

\* \* \* \* \*